US011639919B1

(12) United States Patent
Rutledge (10) Patent No.: US 11,639,919 B1
(45) Date of Patent: May 2, 2023

(54) HEADSPACE GAS MONITOR

(71) Applicant: Dynamic Ratings Pty. Ltd., Glen Waverley (AU)

(72) Inventor: Christopher M. Rutledge, Munford, TN (US)

(73) Assignee: Dynamic Ratings Pty. Ltd., Glen Waverley (AU)

( * ) Notice: Subject to any disclaimer, the term of this patent is extended or adjusted under 35 U.S.C. 154(b) by 249 days.

(21) Appl. No.: 17/133,704

(22) Filed: Dec. 24, 2020

Related U.S. Application Data (60) Provisional application No. 62/954,045, filed on Dec. 27, 2019.

(51) Int. Cl.
  *G01N 33/00* (2006.01)
  *G08B 21/18* (2006.01)
  *G01N 1/24* (2006.01)

(52) U.S. Cl.
  CPC ........... *G01N 33/0004* (2013.01); *G01N 1/24* (2013.01); *G08B 21/182* (2013.01)

(58) Field of Classification Search
  CPC .............................. G01N 1/24; G01N 33/0004
  USPC ......................................................... 137/99
  See application file for complete search history.

(56) References Cited

U.S. PATENT DOCUMENTS

| | | | |
|---|---|---|---|
| 6,365,105 B1 * | 4/2002 | Waters | G01N 30/20 422/70 |
| 6,526,805 B1 * | 3/2003 | Babes-Dornea | G01N 33/2841 96/5 |
| 6,968,728 B2 * | 11/2005 | Gilbert | G01N 33/2841 340/870.18 |
| 7,474,186 B2 | 1/2009 | Altmann | |
| 7,747,417 B2 | 6/2010 | Lamontagne | |
| 7,869,167 B2 * | 1/2011 | Wakchaure | H01F 27/14 361/37 |
| 8,738,301 B2 | 5/2014 | Frotscher et al. | |
| 9,194,857 B2 * | 11/2015 | Mahoney | G01N 33/28 |
| 9,419,430 B1 * | 8/2016 | Tostrud | G06Q 10/0635 |
| 9,613,275 B2 | 4/2017 | Yang | |
| 10,495,622 B2 * | 12/2019 | Robinson | F15D 1/02 |
| 2003/0164479 A1 * | 9/2003 | Goedde | H01B 3/20 252/570 |
| 2015/0127277 A1 | 5/2015 | Desai et al. | |
| 2015/0192551 A1 * | 7/2015 | Peterson | G01N 21/85 73/23.37 |
| 2017/0082595 A1 | 3/2017 | Pruente et al. | |

\* cited by examiner

*Primary Examiner* — John Fitzgerald
(74) *Attorney, Agent, or Firm* — Boyle Fredrickson, S.C.

(57) ABSTRACT

An adapter for use in monitoring the deterioration of an oil insulated transformer due to pyrolysis that allows for an alarm to be generated at the desired ppm values is provided. The adapter is configured to sample the headspace of the main transformer tank as well as the adjacent compartments of a transformer and pass it over a common sensor to check for gases indicative of pyrolysis. During this constant monitoring process, the device will alert the end user when there is an increase in monitors gases. This will allow the owner to take the transformer off line and perform other diagnostic tests to determine the extent of damage to the equipment.

17 Claims, 5 Drawing Sheets

HEADSPACE GAS MONITOR

CROSS-REFERENCE TO RELATED APPLICATIONS

This application claims priority to U.S. Provisional Patent Application Ser. No. 62/954,045, filed Dec. 27, 2019, the entirety of which is herein incorporated by reference,

FIELD OF THE DISCLOSURE

This disclosure relates generally to a system for detecting increases in the total level of hydrogen in the head space of an oil filled electrical asset for detection of a developing fault condition. In particular, the disclosure is directed to a system comprising adapters and manifolds to combine gases from multiple compartments within the oil filled electrical asset for testing hydrogen levels at a common sensor. A method of detecting such hydrogen level is also disclosed.

BACKGROUND OF THE INVENTION

Dissolved gas analysis ("DGA") and combustible gas detection has long been the standard test in the utility industry for the diagnosis and early detection of developing fault conditions that occur within oil filled electrical equipment. Given the known temperatures at which the various insulating mediums produce combustible gases, a measurement of the types and levels of gases present in a sample of the insulating medium or a measurement of the gases contained within the headspace of electrical equipment can be taken. This measurement provides a reliable indicator to any pyrolysis, e.g. high temperature induced composition, that may be developing.

The method most commonly used to achieve this measurement of gases is dissolved gas analysis ("DGA"). The standard DGA method is performed by obtaining a sample of the insulating medium and sending it to a lab to be tested. The lab then returns the results with a breakdown in parts-per-million ("PPM") of the various gases contained within the sample. Most often, the gases measured are hydrogen, methane, ethane, ethylene and acetylene. Standard threshold limits for each of these gases have been established. Any DGA result of one or more gases exceeding these set limits is an indication of pyrolysis as a result of a developing, localized overheating occurring within the electrical asset or equipment.

More recently, several companies in the industry have begun to develop network connected, or online monitors, which can be attached to the electrical equipment to provide a more constant monitoring of the electrical asset. Most often, this type of online monitor provides a constant monitoring of a composite gas (such as hydrogen and acetylene with each gas making up a percentage of the total gas measured). More sophisticated online monitors can measure up to nine individual gases through periodic sampling of the insulating medium. Both of these types of monitors have proven to be very effective in the detection of problems developing in electrical equipment. However, neither form of currently existing online monitor has proven to be a cost-effective solution to the monitoring of distribution type equipment or equipment with multiple compartments. Once reason for this disadvantage is that the existing online monitoring equipment is limited to only measuring gases in one compartment per monitor. Accordingly, distribution type electrical assets or equipment with multiple compartments require multiple monitors to be installed on a network or multi compartment transformer in order to monitor all compartments. The need for multiple monitors prohibits the current technology from offering a cost-effective solution in such situations. For example, the need for multiple monitors often causes the price of the monitoring to exceed 50% of the cost of the equipment being monitored. Accordingly, a need therefor exists to provide a cost-effective monitoring solution for the diagnosis and early detection of developing fault conditions that occur within oil filled distribution type electrical equipment and equipment having multiple compartments.

Another shortcoming of the current monitoring equipment available is that it is primarily designed to measure dissolved gases in oil. Because of this design, the monitoring equipment is often placed below the oil level of the equipment upon which it is installed. This configuration leaves the monitor susceptible to damage from submersion in flooded transformer vaults. Accordingly, a need also exists to provide a monitoring solution for the diagnosis and early detection of developing fault conditions that occur within oil filled distribution type electrical equipment and equipment having multiple compartments that does not risk monitor submersion.

SUMMARY OF THE INVENTION

This invention is designed to provide a reliable, cost effective solution. for monitoring liquid filled electrical equipment. It is designed to circulate the gas contained in the headspace of the electrical equipment by using specially designed sample adapters and manifolds. These adapters and manifolds allow the gases from multiple compartments to be combined into one measurement line and passed across a sensor that is capable of detecting increases in the total level of hydrogen and alarming should the levels of the gas exceed desired limits. After the gas passes over the sensor, it is then returned to the various compartments of the electrical equipment. This invention has several advantages over gas monitoring systems currently on the market. Because it is only designed to measure gases in the headspace and not gases dissolved in liquids, it is possible to monitor multiple compartments using only one sensor.

In one embodiment of the invention a gas adapter for use in monitoring headspace gas of an oil insulated electrical asset is provided. The adapter includes a body having a first fitting configured to engage a compartment of the electrical asset containing headspace gas. A supply channel extends through the body from a source port disposed within a surface of the first fitting to a first side port disposed in an outer surface of the body. A manual sampling port in fluid communication with the supply fluid channel is also disposed within a surface of the body. The gas adapter also includes a return fluid channel extending through the body from a return port disposed within the surface of the first fitting to a second side port disposed in the outer surface of the body.

In another embodiment of the invention, a gas monitoring system for use with an oil insulated electrical asset having a plurality of compartments is provided. The system includes each compartment of the plurality of compartments of the oil insulated electrical asset being in fluid communication with a gas adapter. Each gas adapter includes a body having a first fitting in fluid communication with a corresponding compartment, a supply fluid channel extending through the body from a source port disposed within a surface of the first fitting to a first side port disposed in an outer surface of the body. A manual sampling port is also in fluid communication with the supply fluid channel and disposed within a surface of the body. A return fluid channel extends through the body from a return port disposed within the surface of the first fitting to a second side port disposed in the outer surface of the body. In addition to the adaptors, the system includes a gas manifold system having a supply manifold and a return manifold, and a gas sensor disposed between the supply manifold and return manifold configured to monitor a sample of combined headspace gas from the plurality of compartments.

The method includes circulating all the gases from multiple compartments over one or more sensors by combining multiple intake and return lines into one main line for measurement and then returning them to the various compartments, which helps develop an equilibrium between all the compartments of the electrical equipment. Accordingly, should a leak or variation in pressure due to temperature changes or the like occur in the smaller compartments, the gas from the larger compartments would be able to maintain positive pressure in the smaller compartments for a much longer period, thereby reducing the possibility of moisture ingress. Such a system and method also allows for the overall pressure of all the separate compartments to be monitored using a single monitoring device.

Because it is designed to measure gases in the headspace, the actual monitor can be placed on top of the electrical equipment, above any possible flooding that may occur.

BRIEF DESCRIPTION OF THE DRAWINGS

A clear conception of the advantages and features constituting the present invention will become more readily apparent by referring to the exemplary, and therefore nonlimiting, embodiments illustrated in the drawings accompanying and forming a part of this specification, wherein like reference numerals designate the same elements in the several views.

In the drawings.

In describing the embodiments of the invention which are illustrated in the drawings, specific terminology will be resorted to for the sake of clarity. However, it is not intended that the invention be limited to be specific terms so selected and it is to be understood that each specific term includes all technical equivalents which operate in a similar manner to accomplish a similar purpose. For example, the words "connected," "attached," or terms similar thereto are often used. They are not limited to direct connection or attachment, but include connection or attachment to other elements where such connection or attachment is recognized as being equivalent by those skilled in the art.

DETAILED DESCRIPTION

The following detailed description is presented to enable any person. skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Figure 1:
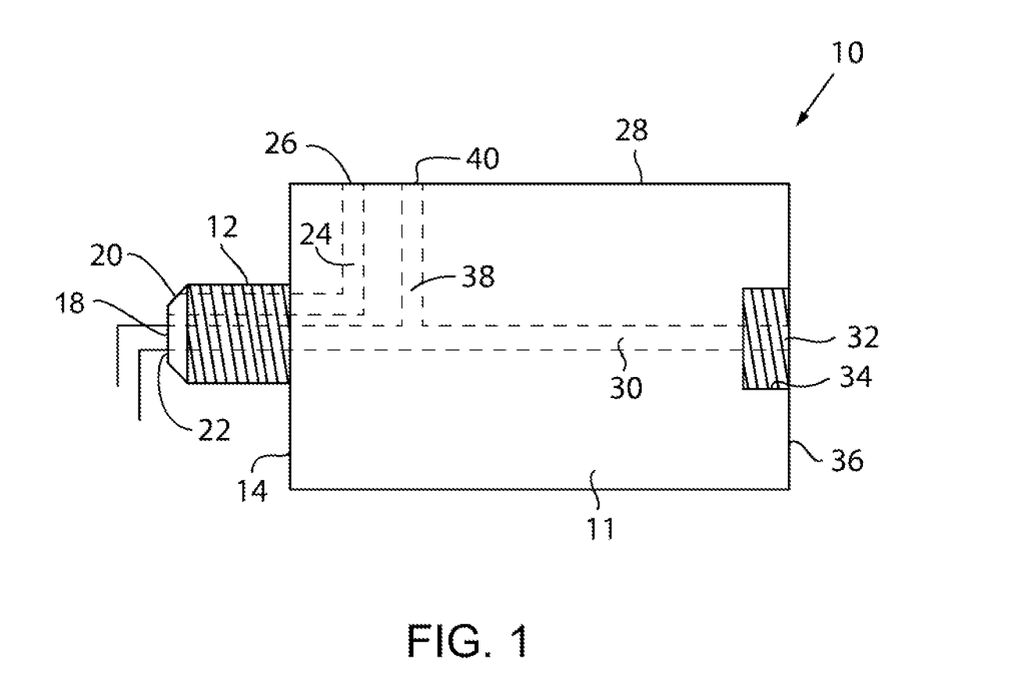
FIG. 1 is a top view of a valve adapter with internal intake and return ports for gases to pass into and out of the headspace of an electrical transformer and adjacent compartments, in accordance with one embodiment of the invention.
Figure 2:
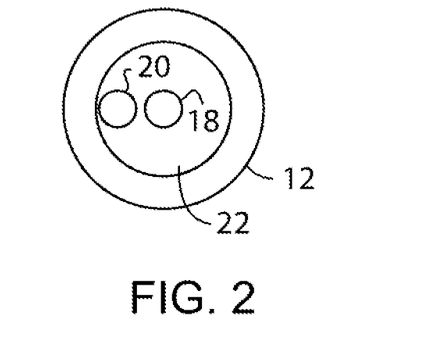
FIG. 2 is an end view of a male threaded fitting of the valve adapter shown in FIG. 1.
Figure 3:
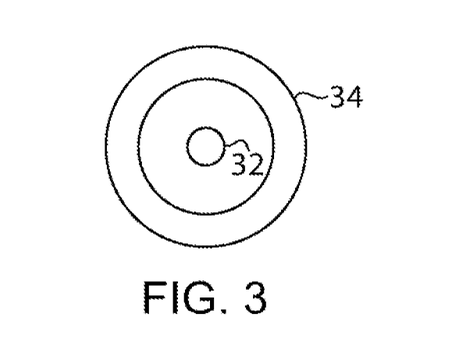
FIG. 3 is an end view of a female threaded fitting of the valve adapter shown in FIG. 1.

With reference now to the drawings, where like numerals refer to like parts throughout, and specifically with reference to FIG. 1, a sample head space adapter 10 is shown. The adapter 10 may representatively be made of brass or other material compatible for use with electrical assets, and may have an approximately 2.0 inch diameter body 11. Adapter 10 comprises a male threaded fitting 12 extending outwardly from a first end 14 that is sized to fit an existing sample port of the electrical asset 16 on which it is to be installed. The male threaded fitting 12 may include two ports, namely a source port 18 and a sensor return port 20; both of which are in fluid communication with the gas contained within in the headspace of the compartment of the electrical asset 16 when the male threaded fitting 12 is affixed to the electrical asset 16. The source port 18 is generally coaxially aligned with a central longitudinal axis of the male threaded fitting 12, while the sensor return port 20 may be off centered. This configuration allows for a sample of headspace gas to be drawn from the gas space within the electrical asset 16, sampled and then returned. An inline pump (not shown in FIG. 1) provides a suction or negative pressure through the source port 18, which returns to the electrical asset 16 through the sensor return port 20. The sensor return port 20 defines an end of internal channel 24, which extends from the outer end 22 of the male threaded fitting 12 of the adapter 10 to a port 26 on an outer side 28 of the adapter 10. The port 26 on the outer side 28 of the adaptor 10 is configured to allow for attachment of a gas return line (not shown in FIG. 1) within a gas line manifold. In one embodiment of the invention, ports 20, 26 may each representatively be 0.1125 inches to allow for threaded attachment to a 0.125 inch gas line fitting. In this configuration, the ports 20, 26 and channel 24, and the gas line which extends therefrom provide for the return of headspace gases to their various compartments after they have been measured through the sensor, as will be described further below.

The source port 18, which also extends through the outer end 22 of the male threaded fitting 12 of the adapter 10, is in fluid communication with an internal channel 30 that extends through the sample adapter 10, to a port 32 disposed within a female threaded fitting 34 located at an opposing end 36 of the adapter 10. This female threaded fitting 34 is sized to accommodate a sample valve, such as a standard ball valve as is commonly originally installed on the electrical asset 16. The internal channel 30 may also include a branch channel 38 that extends from the internal channel 30 to an outlet port 40 on the side 28 of the adapter 10. The port 40 on the side 28 of the adaptor 10 is configured to allow for attachment of a gas return line (not shown in FIG. 1) within a gas line manifold. In one embodiment of the invention, ports 40 and 18 are each threaded to receive a 0.125 inch gas line fitting. In this configuration, the ports 40 and 18 and channels 30, 38 and the gas line which extends therefrom provide for the supply line for headspace gases to be drawn off of their various compartments and be measured through the sensor, as will be described further below. Additionally, in the event that manual sampling of headspace gas is also desired, a sample may be taken directly from the adapter 10, through the sample valve installed at the female threaded fitting 34.

Figure 4:
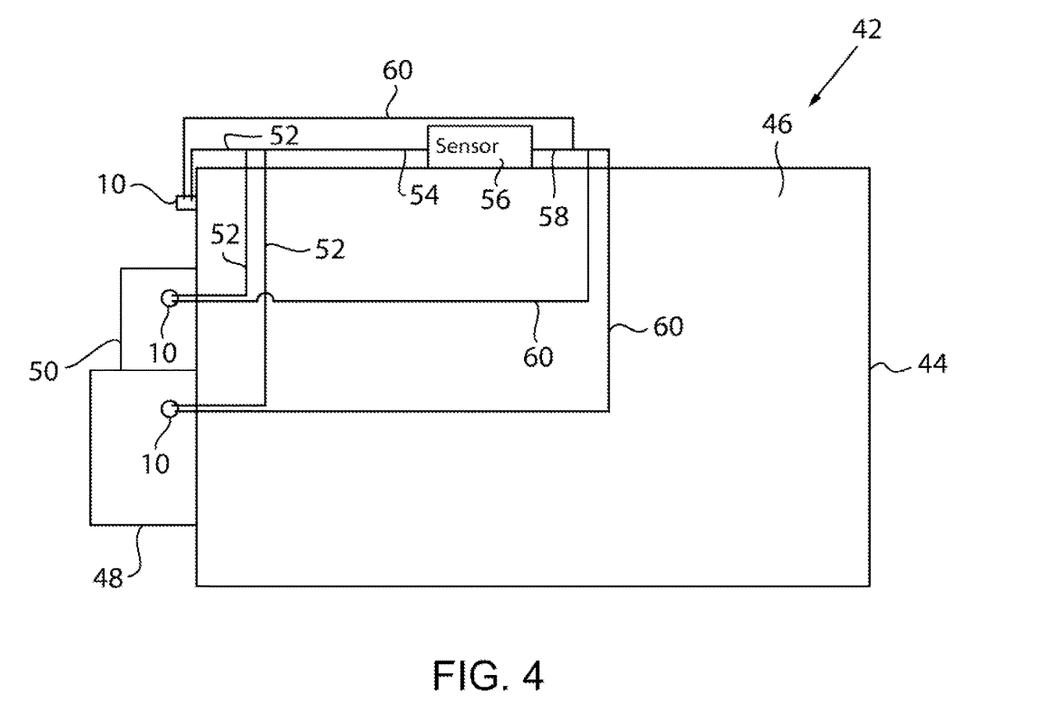
FIG. 4 is a schematic view of a first manifold system for a multiple compartment transformer including the valve adapter of FIG. 1, in accordance with one embodiment of the invention.
Figure 5:
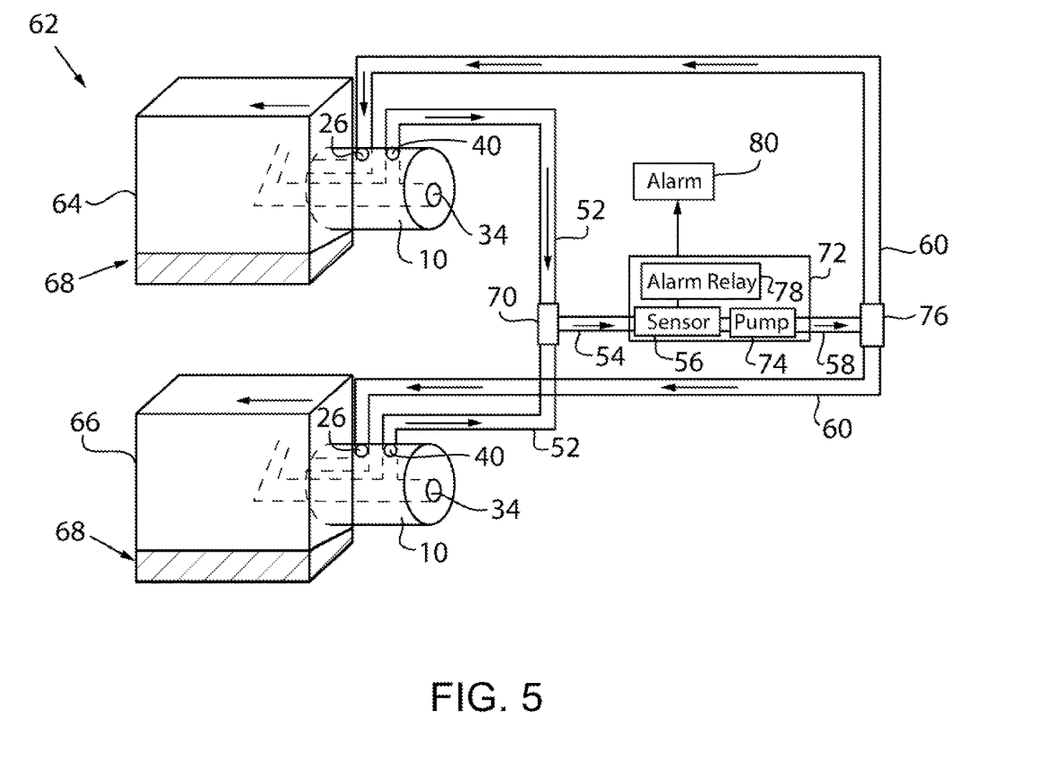
FIG. 5 is a schematic view of a second manifold system for a multiple compartment transformer including the valve adapter of FIG. 1, in accordance with one embodiment of the invention.
Figure 6:
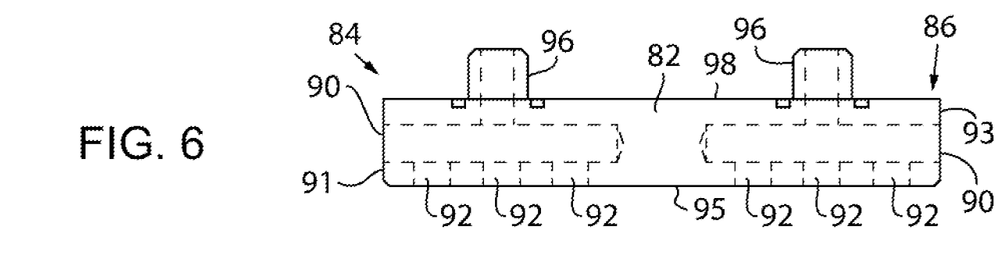
FIG. 6 is a side view of a gas manifold for use in the manifold systems of FIGS. 4 and 5 in accordance with one embodiment of the invention.
Figure 7:
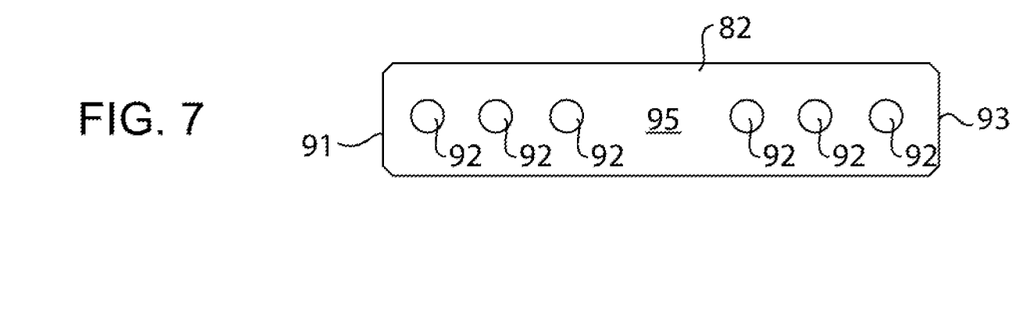
FIG. 7 is a bottom view of the gas manifold of FIG. 6.
Figure 8:
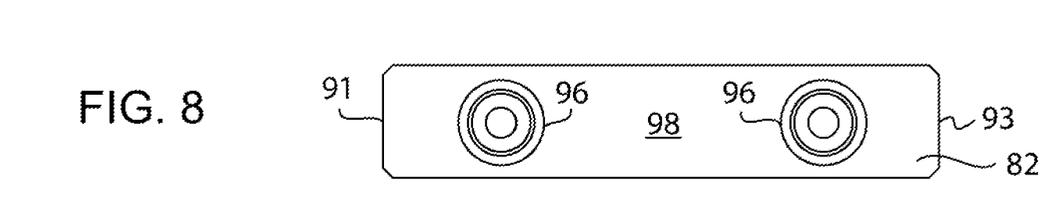
FIG. 8 is a top view of the gas manifold of FIG. 6.
Figure 9:
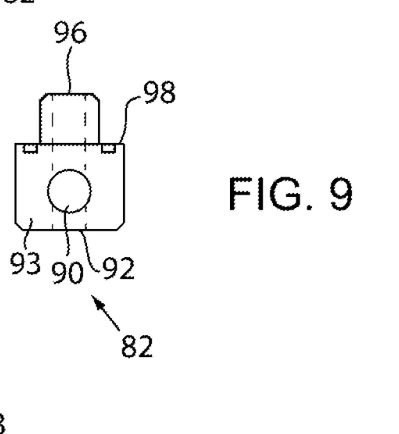
FIG. 9 is an end view of the gas manifold of FIG. 6.

Turning now to FIGS. 4 and 5, and initially FIG. 4, a plurality of adapters 10 are shown integrated into a manifold 42 for sampling headspace gases from an electrical asset in the form of a transformer 44. As shown in FIG. 4, the transformer 44 includes a main tank or main compartment 46, and two additional compartments 48, 50. However, it should be understood that any number of electrical asset compartments are well within the scope of the present invention. Each of the compartments 46, 48, 50 may be attached to an adapter 10 as described above, where the male threaded fitting 12 engages a corresponding connection at each of the respective compartments. During use, the gas located within the compartment 46, 48, 50 of the transformer 42 may be drawn directly from the headspace through the sensor intake port 18, through the internal channels 30, 38, to the outlet port 30 and into an intake line 52 by means of an inline pump (not shown in FIG. 4). In one embodiment of the present inventions, where the transformer 42 or other electrical asset 16 includes multiple compartments, 46, 48, 50, each compartment may provide a discrete intake line 52 within the manifold system 42, which merge into a main test line 54 upstream of the sensor 56. Accordingly, the manifold system 42 allows multiple compartments 46, 48, 50 to be reduced to one main test line 54 to be monitored, as shown in FIG. 6. Moreover, headspace gases contained within each of the discrete compartments 46, 48, 50 of the transformer 44 or alternative electrical asset 16 will be mixed within the manifold system 42, upstream of the sensor 56. As such, the monitoring of gases through the current manifold system 42 will provide a single output for the monitoring of the multi-compartment electrical asset 16.

After the sensor 56 has monitored the combined headspace gas of the transformer 44, the sampled gas exits the sensor 56 to a main return line 58 downstream of the sensor 56. The manifold system 42 then separates the main return line 58 into a plurality of discrete return lines 60, in which one return line 60 travels back to the adapter 10 of each corresponding compartment 46, 48, 50 of the transformer 44. More specifically, each gas return line 60 is in fluid communication with the side port 26 located on the side 28 of the corresponding adapter 10. As the headspace gas is pumped through the manifold system 42, it travels through the return line 60, into the adapter 10 at the side port 26, through the internal channel 24 and then back to the compartment 46, 48, 50 via the gas return port 20 that is located off-center in the male threaded fitting 12. In this configuration, the manifold system 42 forms a closed multi-loop system.

Turning now to FIG. 5, an alternative embodiment of the manifold system 62 is shown in which the electrical asset 16 includes two compartments 64, 66. Placement of the adapter 10 at a height that is greater than the respective oil level 68 in each compartment 64, 66 will prevent the adapter 10 and/or other monitoring equipment from becoming submerged during use. The gas intake lines 52 extend from the side port 40 of each adapter 10 to an intake manifold 70, where the incoming lines are combined into a common main intake line 54. The sensor 56, as previously described, is disposed within a monitor system 72. The sensor 56 may include one or more of infrared (IR) gas sensors, solid state gas sensors, and/or electronic gas sensors for detecting hydrocarbons, such as acetylene, and hydrogen. gases, within the headspace gas. Inline pump 74, located downstream of the sensor 56, generates a negative pressure or suction within the system 62 and draws the headspace gas through the intake lines 52, manifold 70, and main intake 53, before it is monitored at the sensor 56 and returned to the compartments 64, 66. Downstream of the pump 74, gases exit the monitor system 72 and enter the main return line 58, return manifold 76, return lines 60, before entering the compartments 64, 66 via adapters 10.

In the event that the hydrocarbons, such as acetylene, and hydrogen gases, within the headspace gas, exceed a threshold when monitored at the sensor 56, an alarm relay 78 in electrical communication with the sensor 56 may trigger an alarm output 80. The alarm output 80 may be transmitted via wired or wireless connection to a system for monitoring the operating status of the electrical asset 16. In one embodiment, the alarm output 80 may be a tiered alarm that produces a low-level alarm in the event that the hydrocarbons, such as acetylene, and hydrogen gases, within the headspace gas, exceed a first threshold and a high-level alarm or critical alarm in the event that the hydrocarbons, such as acetylene, and hydrogen gases, within the headspace gas, exceed a second threshold that is greater than the first threshold. Furthermore, the alarm output 80 for one or more assets 16 may be provided to an internet connected software, such as a website or SaaS program with remote access for customers, including, a status of the alarm indicating the need to provide maintenance to the asset 16. Additional information may also be included in the internet connected software, such as: the asset rating, actual usage of the asset, operational data collected during the actual usage of the asset, state of the asset heath, or recommended operating or maintenance actions indicative of a respective state of health of the asset 16.

Turning now to FIGS. 6-9, one embodiment of the gas manifold 82 is shown, in which the manifold 82 is mirrored about a midline, having a first side 84 corresponding to the intake manifold 70 and a second side 86 corresponding to the return manifold 76. Each side 84, 86 of the manifold 82 includes a common internal channel 88 that extends from a main line port 90 extending from an end surface 91, 93 respectively to a series of discrete line ports 92 extending from a bottom surface 95. A threaded fitting 96, sized to accommodate a sample valve, such as a ball valve, extends upwardly from a top surface 98 of the manifold. In use, the intake side 84 of the manifold 82 will receive the discrete intake lines 52 at the corresponding line ports 92. The headspace gas will then enter the internal channel 88, where it is mixed and exits the main line port 90 and flows through the main intake line 54 to the sensor 56 in the monitor system 72. After monitoring and upon exiting the inline pump 74, the gas will then flow through the main return line 58, through the main line port 90 on the opposing second side 86 of the manifold, through the internal channel 88, where it will then be split amongst the various discrete line ports 92 and enter the corresponding return lines 60 in order to circulate back to the compartments of the electrical asset 16 via adapters 10.

Sizes of the manifold 82 and corresponding manifold systems 42, 62 may be varied to adapt to different applications. However, in one embodiment the manifold 82 accommodates for 0.125 inch gas lines 52, 54, 58, 60 at ports 90, 92.

It should further be understood that the present invention is well suited for use with electrical assets 16 having multiple compartments, wherein their headspace gas is to be combined and circulated across one sensor chamber and then redistributed hack into the headspace of the asset 16. However, the adapter 10 is also configured for use with a single compartment electrical asset 16, wherein the use of a manifold 80, and/or manifold system 42, 62 need not be included. Furthermore, this entire system may be weather resistant as to inhibit the ingress of atmosphere into the monitor system 72 or manifold systems 42, 62; and also to prevent the escape of any gas from the electrical the monitor system 72 or manifold systems 42, 62.

Additionally, while the system described above has been presented in the context of a multiple compartment transformer, it should be understood that this invention is equally applicable to alternative electrical assets. For example, the adapter 10 and system 42, 62 may be installed on various types of equipment including but not limited to: substation transformers, distribution pad-mounts, regulators, etc.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

I claim:

1. A gas monitoring system for use with an oil insulated electrical asset having a plurality of compartments, the system comprising:
   each compartment of the plurality of compartments of the oil insulated electrical asset in fluid communication with a gas adapter,
   each gas adapter comprising
      a body having a first fitting in fluid communication with corresponding the compartment;
      a supply fluid channel extending through the body from a source port disposed within a surface of the first fitting to a first side port disposed in an outer surface of the body;
      a sampling port in fluid communication with the supply fluid channel disposed within surface of the body; and,
      a return fluid channel extending through the body from a return port disposed within the surface of the first fitting to a second side port disposed in the outer surface of the body;
   a gas manifold system comprising:
      a plurality of gas supply lines, wherein a gas supply line of the plurality of gas supply lines extends from the first side port of each gas adapter to a supply manifold; and,
      a plurality of gas return lines, wherein a gas return line of the plurality of gas return lines extends from a return manifold to the second side port of each gas adapter; and,
   a gas sensor disposed between the supply manifold and return manifold configured to monitor a sample of combined headspace gas from the plurality of compartments.

2. The gas monitoring system of claim 1, wherein the first fitting of the gas adapter body is a threaded male fitting.

3. The gas monitoring system of claim 1, wherein the sampling port of the gas adapter is disposed within a threaded female fitting that is configured to receive a valve at the threaded female fitting.

4. The gas monitoring system of claim 1, wherein the first side port is configured to form a fluid communication with a gas supply line, and the second side port is configured to form a fluid communication with a gas return line.

5. The gas adapter of claim monitoring system of claim 1, wherein the first fitting engages a compartment of the electrical asset at a height greater than that of an oil contained within the compartment.

6. The gas monitoring system of claim 1, further comprising an inline pump between the sensor and the return manifold.

7. The gas monitoring system of claim 1, wherein the sampling port of each gas adapter is disposed within a threaded female fitting that is configured to receive a valve at the threaded female fitting.

8. The gas monitoring system of claim 1, wherein the first fitting of the gas adapter engages the corresponding compartment of the electrical asset at a height greater than that of an oil contained within the compartment.

9. The gas monitoring system of claim 1, wherein the source port of the gas adaptor is coaxially aligned along a central longitudinal axis of the first fitting.

10. The gas monitoring system of claim 9, wherein the return port is positioned between the source port and an outer edge of the first fitting.

11. The gas monitoring system of claim 1, wherein the supply manifold combines a portion of headspace gas from each of the plurality of compartments to form the combined sample of headspace gas from the plurality of compartments.

12. The gas monitoring system of claim 11, wherein the return manifold divides the combined sample of headspace gas into a plurality of return portions, each of which is provided to one gas return line that extends from the return manifold to the second side port of the corresponding gas adapter.

13. The gas monitoring system of claim 1, wherein the gas sensor is configured to identify the parts per million of a hydrocarbon or hydrogen gas in the sample of headspace gas from the plurality of compartments.

14. The gas monitoring system of claim 13, wherein the gas sensor is selected from a group comprising one or more of an infrared gas sensor, a solid state gas sensor, and an electronic gas sensor.

15. The gas monitoring system of claim 13, further comprising an alarm relay to transmit an alarm signal when the parts per million of the hydrocarbon or hydrogen gas in the sample of headspace gas from the plurality of compartments exceeds a predetermined threshold.

16. The gas monitoring system of claim 15, wherein the predetermined threshold is indicative of pyrolysis occurrence in at least one compartment of the electrical asset.

17. The gas monitoring system of claim 16, wherein the alarm signal indicates a severity of the pyrolysis occurrence in at least one compartment of the electrical asset.

* * * * *